United States Patent [19]

Shibasaki

[11] Patent Number: 5,170,285
[45] Date of Patent: Dec. 8, 1992

[54] SEMITRANSPARENT SLIDE AND FILTER COMBINATION FOR A MICROSCOPE

[75] Inventor: Michiro Shibasaki, Mitaka, Japan

[73] Assignee: Senko Medical Instruments Mfg. Co., Ltd., Tokyo, Japan

[21] Appl. No.: 845,362

[22] Filed: Mar. 5, 1992

Related U.S. Application Data

[63] Continuation of Ser. No. 476,484, filed as PCT/JP89/00729, Jul. 20, 1989, abandoned.

[30] Foreign Application Priority Data

Nov. 9, 1988 [JP] Japan .................. 63-282768

[51] Int. Cl.$^5$ .............. G02B 21/34; G02B 5/02; G02B 1/00
[52] U.S. Cl. ............... 359/396; 359/599; 428/323; 428/426
[58] Field of Search .......... 350/534, 535, 536; 428/323, 426; 359/396, 398, 599

[56] References Cited

U.S. PATENT DOCUMENTS

| | | | |
|---|---|---|---|
| 1,996,141 | 4/1935 | Broadhurst et al. | 350/535 |
| 2,801,568 | 8/1957 | Dakin . | |
| 3,527,151 | 9/1970 | Harrison | 359/599 |
| 3,609,000 | 9/1971 | Miyano | 350/126 |
| 3,704,477 | 11/1973 | Weichselbaum | 350/534 |
| 4,087,154 | 5/1978 | Menzel | 350/534 |
| 4,395,493 | 7/1983 | Zahniser et al. . | |
| 4,679,914 | 7/1984 | Rosenberg | 350/534 |
| 4,843,231 | 6/1989 | Culoyannis et al. | 250/223 B |
| 4,906,083 | 3/1990 | Sattler | 350/536 |

FOREIGN PATENT DOCUMENTS

| | | |
|---|---|---|
| 0109208 | 5/1984 | European Pat. Off. . |
| 2180951 | 4/1987 | United Kingdom . |

OTHER PUBLICATIONS

*Science*, Apr. 1, 1955, vol. 121, No. 3144, pp. 474–475 "Improved Adhesion and Visibility . . ."

*Primary Examiner*—Jon W. Henry
*Attorney, Agent, or Firm*—Wegner, Cantor, Mueller & Player

[57] ABSTRACT

A slide is arranged to be semitransparent to scatter the light emitted from a microscope to optically eliminate the outlines of pores of a filter. Material such as cell, nuclei or extracellular materials is captured on the top surface of the filter by filtration. A specimen preparation can be made by placing the filter with the material thereon on the semitransparent slide. A metal evaporation layer, so-called multicoating, can be positioned on the surface of a cover glass, so that the material can be more clearly recognized, especially at high magnification.

4 Claims, 2 Drawing Sheets

SEMITRANSPARENT SLIDE AND FILTER COMBINATION FOR A MICROSCOPE

This application is a continuation of U.S. application Ser. No. 07/476,484 filed as PCT/JP89/00729, Jul. 20, 1989, now abandoned.

TECHNICAL FIELD

This invention relates to a slide which is made to be semitransparent, a cover glass whose top surface is multicoated, and a method of preparing a specimen preparation. By placing a filter, which, in advance, has collected material such as cells by filtration, on a semitransparent slide, a specimen preparation can be prepared.

BACKGROUND ART

In the past, a preparation is usually made by smearing material such as cells on a slide glass. According to this method, the material is captured by excoriation or centesis and then smeared on a slide glass.

Then the slide glass with the material thereon is preserved in, for example, dyeing solution. Thereafter a mounting medium is applied thereon to seal the material, and a cover glass is placed thereon.

In this prior art, the work to smear the material on the slide glass is completed by hand, thus the material could easily be destroyed and deformed. Further, when the material is preserved in the solution, much of it drops from the slide glass into the solution. Also, a lot of expreience and skill are required to accomplish this smear method.

To make the preparation easier, Japanese Patent Application No. 61-250188, for example, introduces a new method wherein a suspension medium including material is drawn through a polycarbonate membrane filter, which is transparent, has a thickness about 5 to 10 μm and innumerable microscopic pores are created through the filter. After the material is captured on the filter as the suspension medium is drawn through the pores, a number of needed solutions such as dyeing solutions are applied to the material.

According to this new method, since it is unnecessary to smear the material on the slide glass, the problem that the material is destroyed and deformed can be eased and the outlines of the material can better be recognized as they naturally are.

After the dyeing process is completed, the material is supposed to be placed on a slide glass to prepare a specimen preparation. To make the preparation with this new method, however, either the material has to be transferred to the slide glass (see U.S. Pat. No. 4,395,493), or the filter with the material thereon should be placed on the slide glass and the filter has to be melted by a melting liquid, eliminating the pores and leaving the material on the slide glass.

When the material collected on the filter is transferred on the slide glass, which is done by pressing the filter onto the slide glass as to transcribe the material to the slide glass, much of it is destroyed and deformed by the pressure. Further, by this so-called transcribing process, it is possible that only a small percentage of the whole material can be transcribed onto the slide glass. As far as the other method is concerned, the material would be shrunken and faded by the melting liquid.

Concerning these problems, it is desirable that a specimen preparation can be prepared only by placing a filter with material thereon onto a slide glass, eliminating the need for transcribing and melting processes. However, when a specimen preparation is prepared by this method, the outlines of the pores of the filter are recognized, and they double with the outlines of the material, so that an examination of the material will be inaccurate.

Therefore, the major object of the present invention is to optically eliminate the pores of the filter, to eliminating the need for the transcribing and melting processes, to provide a slide (not necessarily a glass slide) and a cover glass that enable you to accurately examine the material, and to provide a method of preparing a specimen preparation using the semitransparent slide.

DISCLOSURE OF INVENTION

Figure 1:
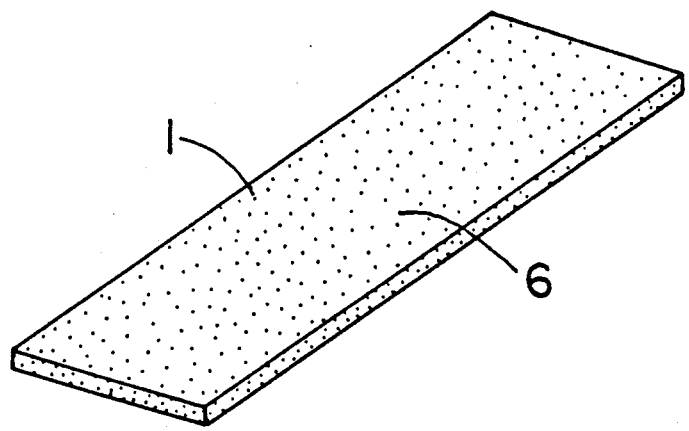
FIG. 1 is a perspective view of a preferred embodiment of a semitransparent slide according to the present invention.

To accomplish the object of the present invention, a slide 1 is made to be semitransparent to scatter the light emitted from a microscope to optically eliminate the outlines of the pores 4 of a filter 3. That is, optically speaking, the pores 4 are lit so that the degree of lightness of the outlines of the pores 4 becomes similar to that of the surrounding area, so that the pores 4 cannot be recognized. According to the present invention, semitransparency is obtained by actively refracting and scattering the light (that is to say that the light beams are prevented from propagating in the straight direction and they are bent in many directions), which is emitted from a microscipe while the transmittancy of the light is still kept high. It is not obtained by reducing the transmittency of the light.

There may by many ways to do so. For example, it is accomplished by including in a slide a large number of parcticles which have such specific charatristics that the light tramsmittancy thereof is lower than that of a slide or the light refraction thereof is much larger than that of a slide. Of course, the particles could possesses both characteristics at the same time. It is possible to adjust the degree of semitransparency by changing the roughness of the particles.

Another way to effectively refract and scatter the light of a microscope is to position a semitransparent layer 2, on the surface of slide 1, such that the light refraction thereof is larger than that of the slide 1.

The semitransparent layer 2 can be made by including in a transparent macromolecule resin and a innumerable number of articles 6. Said articles 6 being an inorganic material made of, for example, ceramics.

To further effectively refract the light of a microscope, the border surface of the slide 1 and the semitransparent layer 2 can be made rougher. Of course, the light refraction of the slide 1 and the semitransparent layer 2 in this case must be made dissimilar. There are many ways to make the border surface rougher. In one of them, for example, the surface of a roller, that presses and produces a slide 1 or a semitransparent layer 2, can be made rough.

A specimen preparation according to the present invention can be prepared by placing a filter 3 with material thereon on a semitransparent slide. To make a more complete preparation, an organic solvent should be applied on the semitransparent slide, then the filter 3 with the material 5 thereon, a mounting medium, and a cover glass 8 should respectively be placed thereon. This method prevents the formation of air bubbles in the specimen preparation.

According to the present invention, when material on a filter 3 which is placed on a semitransparent slide is examined with a microscope, the slide is illuminated from underneath by the light of a microscope. In such circumstances, since the slide 1 is arranged to be semitransparent, the light emitted thereto is refracted and scattered in various directions. The refracted light emits pores 4 of the filter 3 from various directions, so that the degree of the lightness of the pores 4 becomes similar to that of the surrounding area, resulting in the outlines of the pores 4 being optically eliminated, though they physically still exist.

In the prior art, a slide is transparent and the light transmittancy thereof is high, therefore the light of a microscope advances straight ahead so that the pores 4 of a filter 3 are clearly observed, making the accurate examination of material 5 impossible. According to the present invention, such a problem is eliminated since the light from a microscope refracts and scatters in many directions.

As stated previously, the effective light refraction can be obtained by making the border surface of a slide 1 and a semitransparent layer 2 a rough surface 7, because in this way, the light first refracts at the rough surface 7 and again at the semitransparent layer 2. According to this method, since the light can be refracted effectively, the semitransparent layer 2 can be made thinner and the number of particles included in the semitransparent layer 2 can be minimized, which is advantageous when productivities are concerned.

A semitransparent slide according to the present invention can be made mechanically stronger and therefore it is used for a longer time. This can be accomplished by making the semitransparent layer 2 with a macromolecule resin and the particles 6 included in a semitransparent layer 2 with inorganic materials such as ceramics. By doing so, the chemical, heat and weather resistance of the resin of the semitransparent layer 2 improves. As it is known, the resin can easily be faded by chemicals and repeated use. Also, the mechanical strength of the resin is weaker than glass. Therefore, to include inorganic particles 6 in the resin to eliminate the weakness of the resin is extremely effective to make the semitransparent slide as strong as a slide made of glass.

BEST MODE FOR CARRYING OUT OF THE INVENTION

The details of the present invention are described hereinafter. FIG. 1 shows a preferred embodiment of the present invention. In the preferred embodiment, an innumerable number of particles, made of ceramics, globular shaped powder, pigments, powdered bones and so on, having a light refraction dissimilar to the slide 1 and a characteristic of a remarkable light refraction, are included in the material of slide 1 to make the transparent slide 1 a muddy white color. The light emitted from a microscope is refracted inside the semitransparent slide, and the refracted light emits the pores 4 of a filter 3 from various directions, so that the pores 4 cannot be recognized when material on the filter 3 are examined. The slide 1 can be colored other than white such as light blue.

Figure 2:
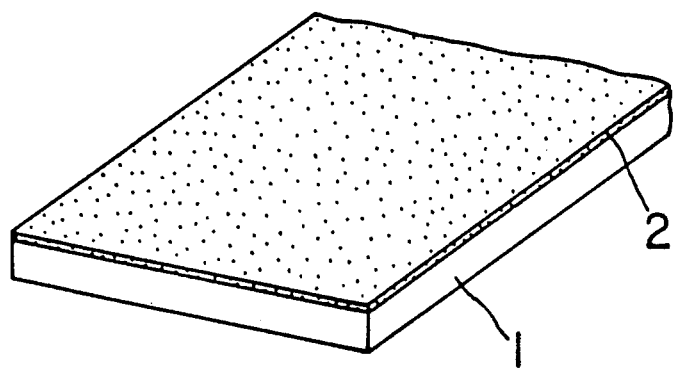
FIG. 2 is a perspective view of another preferred embodiment of a semitransparent slide according to the present invention.

FIG. 2 shows another preferred embodiment of the present invention. A semitransparent layer 2, in this case, is positioned on a transparent slide 1 made of macromolecule resin. The method of making the macromolecule resin semitransparent is not limited but, for example, may be done by crystallizing the macromolecule to white or by blending other resins in the macromolecule resin.

According to this preferred embodiment, the light is refracted by the semitransparent layer 2 and the similar effect pursued by the first preferred emobodiment can be achieved. This semitransparent layer 2 is crystallized in white and an innumerable number of particles 6 of ceramics are contained therein, so that the refraction and the scattering of the light can effectively be accomplished. By adding an emitting material or a layer to the surface of each particle, the light can more effectively be refracted and scattered.

Figure 3:
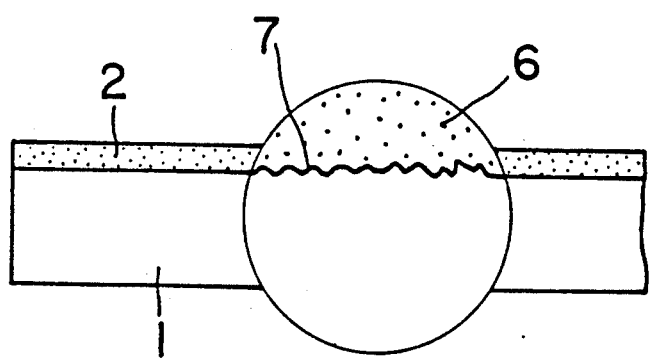
FIG. 3 is a sectional view of another preferred embodiment of a semitransparent slide according to the present invention.

FIG. 3 shows an another preferred embodiment of the present invention, wherein the border surface of the slide 1 and the semitransparent layer 2 is made to be a rough surface 7. Thus, the light is refracted by the rough surface 7, and it is further refracted by the semitransparent layer 2, so that the light can actively be refracted and scattered. Also, the slide 1 and the semitransparent layer 2 can more firmly stick to each other.

The rough surface 7 can be made by blasting sand on the surface of the slide 1 or by soaking the slide 1 in chemicals such as a fluoride acid.

The semitransparent layer 2 can be positioned on the surface of the slide 1 by such methods as wherein the macromolecule resin is pressed and hardened on the slide 1, applied or sprayed to the surface of the slide 1, transcribed onto the slide 1, or the slide 1 is soaked in the macromolecule resin. In this case, for example, the thickness of the slide 1 may be about 1 mm and that of the semitranparent layer 2 less than 0.2 mm to obtain a total thickness of the semitransparent slide less than 1.2 mm to meet the requirements of JIS (Japanese Industrial Standard).

To obtain the object of the present invention, a high transmittancy and an active refraction and acattering are required by a transparent slide. The semitransparent slide described above possesses more than 60~80 percent of transmittancy and a highly active light refraction caused by the semitransparent layer 2, so that the pores 4 of the filter 3 can be completely erased optically. It is a highly remarkable slide.

The shape of the semitransparent slide according to the present invention is not limited to those described as the preferred embodiments. A semitransparent slide can be arranged such as a sandwich-like shape by making another transparent layer on the semitransparent layer 2. In this case, the thickness of the semitransparenet layer 2 may be prepared to be about 0.2 mm and that of transparent layer may be about 0.01 mm, making the total thickness of the semitransparent slide, including the transparent slide 1 about 1.2 mm. By making the semitransparent slide a sandwich-like shape and adjusting the thickness of the transparent layer, the resolution becomes better and the outlines of material can clearly be recognized, so that an examination of the material becomes easier and accurate.

Further, a semitransparent layer 2 can be positioned not only on the top surface of the slide 1 but also on the under surface, or both top and under surfaces of the slide 1. The characteristics of the present invention are that a slide 1 is made to be semitransparent to efficiently refract and scatter the light emitted from a microscope to optically erase the pores 4 of a filter 3. The method of making the slide semitransparent is not limited at all.

Semitransparent as described herein includes one that looks opaque by naked eyes but transmits light therethrough.

A slide 1 here includes such that can place things such as material and filter 3 thereon, and it is not limited to a glass slide. Therefore, it includes, for example, products of macromolecule resin and ceramics.

Further, a slide here includes one that can be recognized as opaque or transparent depending on the visual angle.

Figure 4:
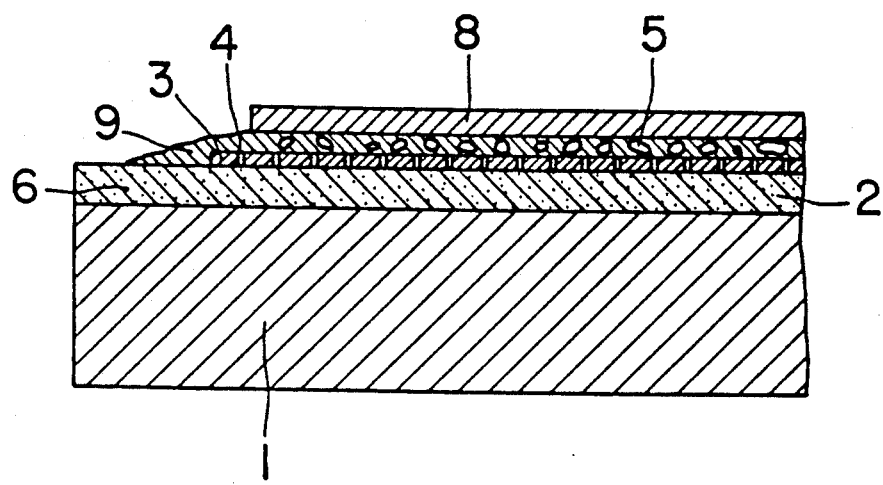
FIG. 4 is a sectional view of a preparation made by a method of preparing a specimen preparation according to the present invention.

FIG. 4 shows a specimen preparation made with a semitransparent slide according to the present invention and a filter 3. It is prepared by the following procedures. First, xylol is applied on the semitransparent slide and a filter 3 with material thereon is placed on it. The xylol flows into the pores 4 and pushes the air out of the pores 4. Therefore, the whole material 5 can be positioned at the same level on the filter 3 and air bubbles cannot be formed, so that examination of the material becomes easy and accurate.

Then, a mounting medium 9 is applied to the filter 3 and a cover glass 8 is placed thereon, completing the procedure. At this point, the xylol applied previously evaporates and it is replaced by the mounting medium 9, so that the filter 3 and the slide 1 are firmly stuck to each other, and the material 5 can be completely sealed.

The method of making a preparation is not limited to the one explained above. For example, any other appropriate mediums such as immersion oil can be accordingly applied thereon.

A characteristic of a method of making a preparation according to the present invention is that where a filter 3 with material collected thereon is placed on the semitransparent slide. The effect is that the light emitted from a microscope is actively refracted and scattered, so that the pores 4 of the filter 3 are optically erased, making the accurate and easy examination of the material 5 possible.

The material of a filter 3 is not limited. A polyester membranfilter, a polycarbonate membrane filter, having a thickness thereof of about 10 μm with an innumerable number of pores 4 therethrough, the diameter of the pores 4 being a few micron, and so-called a honeycomb-like filter which is made of a thin alumina having innumerable number of honeycomb-like pores therethrough are some of the filters preferably used as a membrane filter 3.

Figure 5:
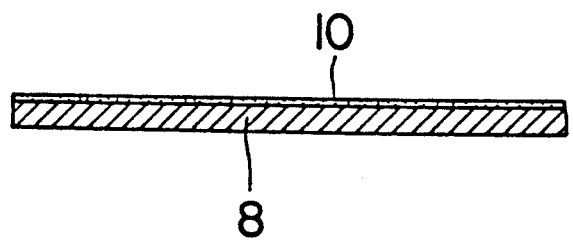
FIG. 5 is a sectional view of a preferred embodiment of a cover glass according to the present invention.

FIG. 5 shows a cover glass 8 according to the present invention. A metal evaporation layer 10, the thickness thereof being in microns to angstroms and is formed of metal molecules such as magnesium fluoride, aluminum and zirconium oxide, is placed on the transparent cover glass 8 by a vacuum evaporation, so-called multicoating. According to a test, this cover glass is especially effective when material is to be examined at high magnification, since the multi coating layer, the metal evaporation layer 10, prevents the light reflection when the light comes out from the cover glass 8 to the air. This improves the light transmittancy of the cover glass 8.

As stated previously, according to the present invention, a slide is made to be semitransparent, so that the outlines of the pores of a filter cannot be observed. Therefore, neither a so-called transcription or a melting procedure become unnecessary, and material on the filter can be recognized clearly.

By arranging the border surface between the slide and the semitransparent layer, the light emitted from a microscope can be more effectively refracted and scattered.

By making a semitransparent layer with a macromolecule resin and including inorganic particles therein, the degree of the light refraction becomes higher, the chemical, heat and whether resistance improves, and mechanical strength advances, so that the durability of the semitransparent slide becomes as tough as the one made of glass.

According to the method of making a specimen preparation, a filter with material thereon is placed on a semitransparent slide, which eliminates the need for a smearing process, so that the material cannot be destroyed or deformed and they do not even drop in a dyeing from the filter. This enables you to examine the material without error.

Another effect of the method of making a preparation according to the present invention is that it does not require either a lot of expreience or good skill and anyone could make the preparation without much difficulty. This improves the efficiency of preparing specimen preparations.

Further, by making a metal evaporation particle layer on a cover glass, material can be examined more clearly especially when they are recognized at high magnification.

I claim:

1. A slide and filter combination for a microscope comprising:

a semitransparent slide comprising one or a plurality of layers such that said slide has two opposed outer flat surfaces; and a filter having a porous surface placed adjacent to one of said opposed outer flat surfaces of said semitransparent slide such that light of a microscope is transmitted through said slide and said filter to permit observance of a specimen placed on said filter by a user;

wherein at least one layer of said slide has a semitransparent portion including means for refracting and scattering light transmitted therethrough such that pores of the filter are not visible to a user.

2. The combination according to claim 1, wherein said slide comprises a layer which is crystallized to appear white.

3. The combination according to claim 1, wherein said semitransparent portion is composed of a macromolecule being crystallized to appear milky in color.

4. The combination according to claim 1, wherein the semitransparent slide comprises a transparent layer composed of a transparent material and a semitransparent layer opposed adjacent to said transparent layer, said semitransparent layer composed of a transparent material containing particles embedded therein, said particles having a lower light transmittance than said transparent material, said particles refracting and scattering light transmitted through said semitransparent layer.

* * * * *